United States Patent
Mulzer et al.

(10) Patent No.: US 9,466,208 B2
(45) Date of Patent: Oct. 11, 2016

(54) DEVICE AND METHOD FOR IDENTIFYING A COLLISION IN A MEDICAL INSTRUMENT

(71) Applicants: Harald Mulzer, Speinshart (DE); Matthias Schirbl, Freihung (DE)

(72) Inventors: Harald Mulzer, Speinshart (DE); Matthias Schirbl, Freihung (DE)

(73) Assignee: Siemens Aktiengesellschaft, München (DE)

( * ) Notice: Subject to any disclaimer, the term of this patent is extended or adjusted under 35 U.S.C. 154(b) by 122 days.

(21) Appl. No.: 14/184,715

(22) Filed: Feb. 20, 2014

(65) Prior Publication Data

US 2014/0232527 A1    Aug. 21, 2014

(30) Foreign Application Priority Data

Feb. 20, 2013   (DE) .................. 10 2013 202 703

(51) Int. Cl.
*G08C 19/00* (2006.01)
*A61B 6/10* (2006.01)
*A61B 6/00* (2006.01)
*H01H 15/14* (2006.01)

(52) U.S. Cl.
CPC ............... *G08C 19/00* (2013.01); *A61B 6/102* (2013.01); *A61B 6/4441* (2013.01); *H01H 15/14* (2013.01)

(58) Field of Classification Search
None
See application file for complete search history.

(56) References Cited

U.S. PATENT DOCUMENTS

| | | | |
|---|---|---|---|
| 5,570,770 A | 11/1996 | Baaten et al. | |
| 5,705,190 A | 1/1998 | Broad et al. | |
| 6,696,652 B1 | 2/2004 | Spies | |
| 6,822,174 B1 | 11/2004 | Spies | |
| 2003/0173197 A1 | 9/2003 | Meagher et al. | |
| 2008/0185851 A1* | 8/2008 | Evans | B60R 19/18 293/120 |
| 2013/0163728 A1* | 6/2013 | Silberklang | A61B 6/037 378/177 |

FOREIGN PATENT DOCUMENTS

| | | |
|---|---|---|
| CN | 1205629 A | 1/1999 |
| CN | 1351753 A | 5/2002 |
| CN | 1771571 A | 5/2006 |
| DE | 8532381 U1 | 2/1986 |
| DE | 10249579 A1 | 5/2004 |
| GB | 2324199 A | 10/1998 |

OTHER PUBLICATIONS

German Office Action for German Application No. 10 2013 202 703.6, mailed Sep. 24, 2013, with English Translation.
Chinese Office action for related Chinese Application No. 201410057215.7, dated Jul. 24, 2015 with English Translation.

\* cited by examiner

*Primary Examiner* — Daniell L Negron
(74) *Attorney, Agent, or Firm* — Lempia Summerfield Katz LLC

(57) ABSTRACT

A device and an associated method for identifying a collision in a medical instrument are provided. The device includes a carrier module of the medical instrument, a housing cladding module that is detachably connected to the carrier module at at least one connection site, and at least one switching element arranged on the carrier module at a distance from the connection site. A partial portion of the housing cladding module has a spring-like flexible design in order to be pressed in the direction of the switching element during a collision with an object.

20 Claims, 2 Drawing Sheets

DEVICE AND METHOD FOR IDENTIFYING A COLLISION IN A MEDICAL INSTRUMENT

This application claims the benefit of DE 10 2013 202 703.6, filed on Feb. 20, 2013, which is hereby incorporated by reference in its entirety.

FIELD

The present embodiments relate to a device and a method for identifying a collision of a medical instrument with an object.

BACKGROUND

By way of example, a medical instrument is known from the patent document U.S. Pat. No. 5,570,770. Medical instruments for medical diagnosis or therapy may have an x-ray emitter and an x-ray detector, each being within a housing. The x-ray emitter and the x-ray detector are arranged at a distance from one another, with a patient to be examined or to be treated being placed between the x-ray emitter and the x-ray detector. The x-ray emitter and the x-ray detector are positioned relative to the body of the patient such that an image of a desired cross-section of the body interior may be recorded. The alignment and positioning of the medical instrument may be undertaken with the aid of a motor-driven drive.

Such instruments may be equipped with a C-arm (e.g., with an arcuate holder that may be rotated about several planes with the aid of a guide-rail system). During the use of the medical instrument, a moved part (e.g., the x-ray detector) may come close to the object to be examined in order to achieve the desired image quality. The x-ray detector has a comparatively large frontal area for receiving the x-ray beams, and every point on this frontal area or on a circumference may come into contact with the patient to be examined. Such a collision may occur in any movement direction of the x-ray detector. This is undesirable, and therefore, an instrument of this type is equipped with a detection device for identifying the collision with an object.

If contact between the movable part of the instrument and the object is identified, the movement of the aforementioned instrument may be stopped in order thereby to minimize the severity of the aftermath of a collision. In the aforementioned patent document U.S. Pat. No. 5,570,770, a medical x-ray instrument that is equipped with an electrical detection device for identifying collisions is described. Sensor devices in the instrument are configured to measure the current or power taken up by the drive motor. These variables provide an indication of the current force exerted on the movable part. This current value may be compared to an expected value for the aforementioned force. If the difference between the current value and the expected value exceeds a predetermined threshold, the assumption is made that the movement of the movable part is impeded by an object and hence that a collision is taking place. Accordingly, an alarm signal is generated, and the movement is stopped.

Housing claddings of movable medical instruments or parts of claddings, in which a collision with an object has an effect on an electrical switch or on electrically switchable contacts, are also known. By way of example, such housing claddings are mounted resiliently, with the positional displacement thereof by a collision being identified. The switching signals obtained therefrom are used to switch off a movement of the medical instrument.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a device and an associated method that may detect a collision of a medical instrument with an object are provided.

Cladding of the medical instrument is attached in a partly movable manner to a support part situated therebelow in regions at risk of colliding. Microswitches are attached under the cladding on the support part in the collision region. The microswitches are switched by the cladding during a collision. As a result of using cladding made of an elastic material, the resilient property of the cladding established thereby is employed to serve the microswitch situated therebelow as resilient actuation element.

In one embodiment, a device for identifying a collision in a medical instrument includes a carrier module of the medical instrument and a housing cladding module that is detachably connected to the carrier module at at least one connection site. The device also includes at least one switching element that is arranged on the carrier module at a distance from the connection site. A partial portion of the housing cladding module has a spring-like flexible design that may be moved in a direction of the switching element during a collision with an object. One or more of the present embodiments offer the advantage that collision identification may make do without expensive touch-sensitive surfaces or safety edges.

In one embodiment, a bending line is formed in the housing cladding module. The bending line is able to bend the partial portion along the bending line during the collision.

In a further embodiment, the bending line is formed by a thin point of the housing cladding module.

In a further embodiment, at least one switching lug that is able to actuate the switching element may be formed in the partial portion.

The switching element may be a microswitch, by which a colliding movement of the carrier module may be switched off.

The switching lug may be at a predetermined distance from the switching element, as a result of which a switching path is formed.

In one embodiment, the housing cladding module is screwed to the carrier module at the connection site.

The housing cladding module may be formed from a thermoplastic polymer.

In one or more of the present embodiments, a medical instrument with a device is provided.

In one or more of the present embodiments, a method for identifying a collision in a medical instrument with a device is provided. As a result of the collision with the object, the partial portion of the housing cladding module is moved in the direction of the switching element, actuates the switching element, and the switching element triggers a collision signal.

DETAILED DESCRIPTION

Figure 1:
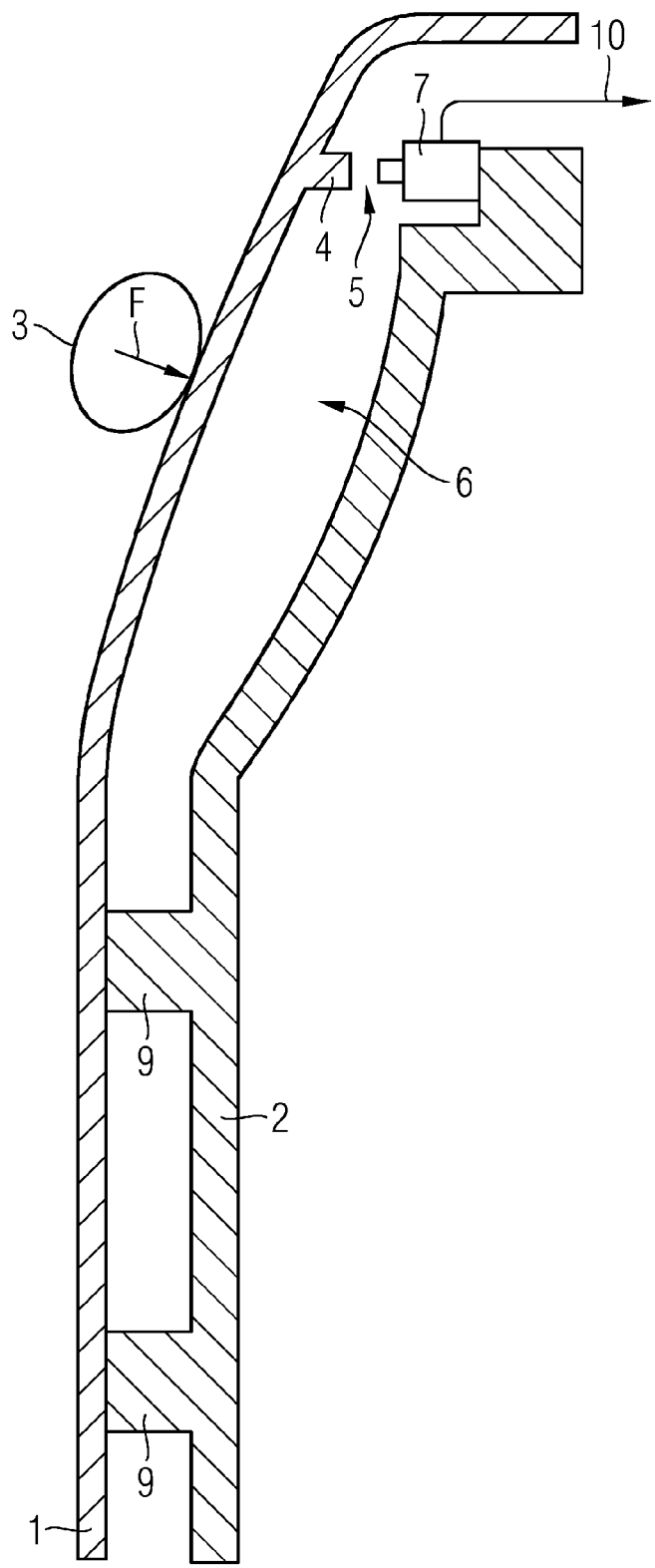
FIG. 1 shows a cross section through one embodiment of a housing cladding module.

FIG. 1 shows a cross-sectional view of part of one embodiment of a medical instrument (e.g., a displaceable C-arm x-ray instrument). A housing cladding module 1 is attached (e.g., screwed) to a carrier module 2 at the connection sites 9 of the carrier module 2. A partial portion 6 of the housing cladding module 1 situated on the right-hand side in the drawing is at risk of colliding. The partial portion 6 is made of a flexible, elastic material (e.g., a thermoplastic polymer) in order to be movable.

One or more switching elements 7 are arranged below the flexible partial portion 6, and the one or more switching elements are fixedly connected to the carrier module 2. In order to actuate the switching element 7, a switching lug 4 is formed in the housing cladding module 1. Before actuating the switching element 7, the switching lug 4 passes over a switching path 5. The switching element 7 may be a microswitch.

As a result of a collision with an object 3, a collision force F is applied to the housing cladding module 1, which brings about a movement of the partial portion 6 in the direction of the switching element 7 and switches the switching element. When switched, the switching element 7 triggers a collision signal 10 that may be processed further in the medical instrument and, for example, stops a movement.

Figure 2:
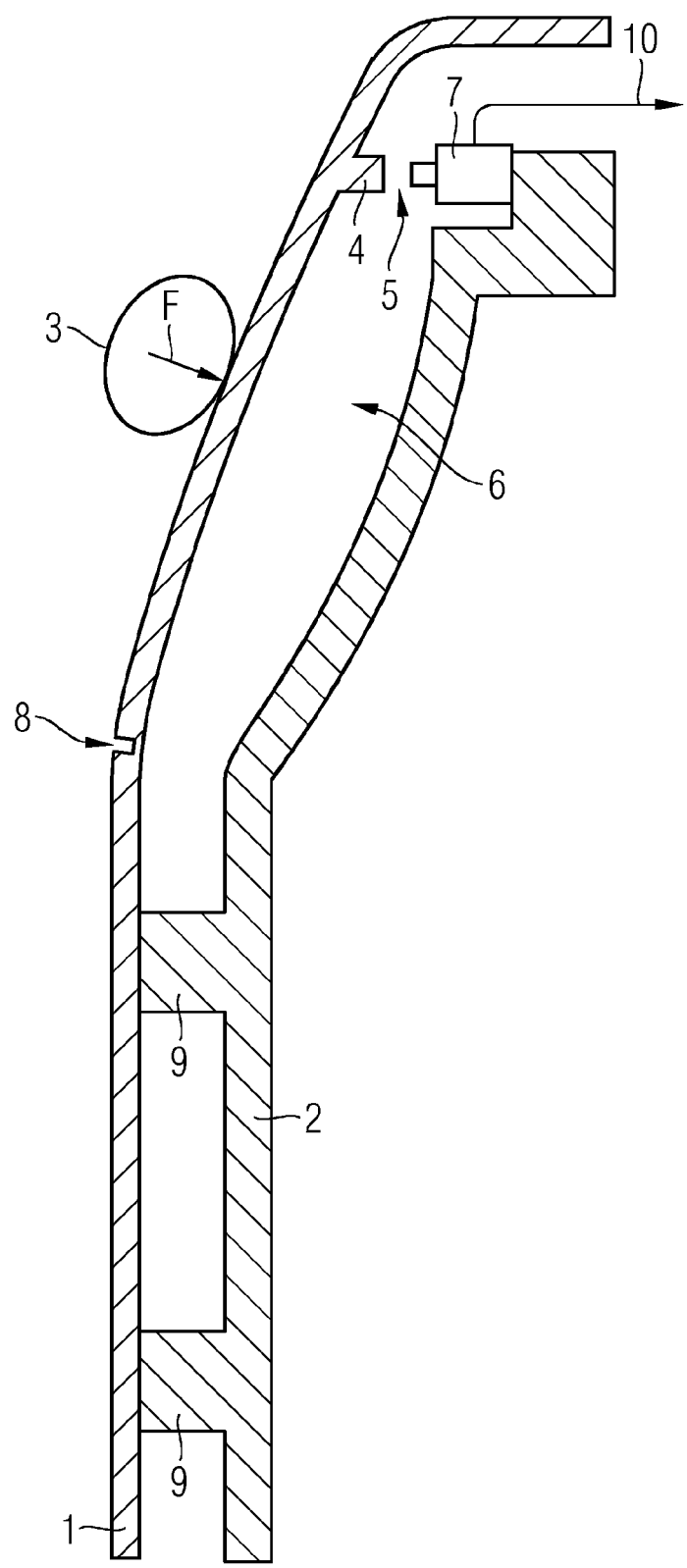
FIG. 2 shows a cross section through one embodiment of a housing cladding module with bending line.

An alternative to the embodiment of FIG. 1 is provided in FIG. 2. FIG. 2 shows the view of part of a medical instrument (e.g., a displaceable C-arm x-ray instrument) in a cross section. A housing cladding module 1 is attached (e.g., screwed) to a carrier module 2 at connection sites 9 of the carrier module 2. The partial portion 6 of the housing cladding module 1 situated on the right-hand side is at risk of colliding. The partial portion 6 is separated from the remainder of the housing cladding module 1 by a bending line 8. The bending line 8 constitutes an intended bending point, about which the partial portion 6 may be bent in relation to the remainder of the housing cladding module 1.

The bending line 8 may be formed by a thin point of the material in the housing cladding module 1. As a result, the housing cladding module 1 may be bent easily along the bending line 8 and in a resilient manner in the direction of the switching elements 7 arranged below the partial portion 6. The switching element or switching elements 7 are fixedly connected to the carrier module 2.

A switching lug 4 is formed in the housing cladding module 1 for actuating the switching element 7. Before actuating the switching element 7, the switching lug 4 is to pass over a switching path 5. The switching element 7 may be a microswitch. An object 3 applies a collision force F to the housing cladding module 1 as a result of a collision therewith, which brings about a movement of the partial portion 6 along the bending line 8 in the direction of the switching element 7. When switched, the switching element 7 triggers a collision signal 10 that may be processed further in the medical instrument. By way of example, a movement of a C-arm is stopped.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for identifying a collision in a medical instrument, the device comprising:
   a carrier module;
   a housing cladding module that is detachably connected to the carrier module at a connection site;
   a switching element that is arranged on the carrier module adjacent to an end of the carrier module at a distance from the connection site; and
   a portion of the housing cladding module positioned between the connection site and an end of the housing cladding module adjacent to the switching element, the portion of the housing cladding module having a spring-like flexible design configured to be pressed in a direction of the switching element during a collision with an object,
   wherein the device is configured to move from an open position to a closed position upon collision with the object, wherein the end of the housing cladding module adjacent to the switching element does not contact the switching element in the open position, and wherein the end of the housing cladding module adjacent to the switching element contacts the switching element in the closed position.

2. The device of claim 1, further comprising a bending line in the housing cladding module, the bending line being configured to bend the portion along the bending line during the collision.

3. The device of claim 2, wherein the bending line is formed by a thin point of the housing cladding module.

4. The device of claim 1, further comprising a switching lug located in the portion of the housing cladding module and configured to actuate the switching element.

5. The device of claim 4, wherein the switching lug is at a distance from the switching element in the open position, as a result of which a switching path is formable.

6. The device of claim 1, wherein the switching element comprises a microswitch, the microswitch being configured to stop a movement of the carrier module.

7. The device of claim 1, wherein the housing cladding module is screwed to the carrier module at the connection site.

8. The device of claim 1, wherein the housing cladding module is a thermoplastic polymer.

9. The device claim 1, wherein the medical instrument is a C-arm x-ray instrument.

10. A medical instrument comprising:
    a device for identifying a collision in a medical instrument, the device comprising:
    a carrier module;
    a housing cladding module that is detachably connected to the carrier module at a connection site;
    a switching element that is arranged on the carrier module adjacent to an end of the carrier module at a distance from the connection site; and a portion of the housing cladding module positioned between the connection site and an end of the housing cladding module adjacent to the switching element, the portion of the housing cladding module having a spring-like flexible design configured to be pressed in a direction of the switching element during a collision with an object, wherein the device is configured to move from an open position to a closed position upon collision with the object, wherein the end of the housing cladding module adjacent to the switching element does not contact the switching element in the open position, and wherein the end of the housing cladding module adjacent to the switching element contacts and the switching element in the closed position.

11. The medical instrument of claim 10, wherein the device further comprises a bending line in the housing cladding module, the bending line being configured to bend the portion along the bending line during the collision.

12. The medical instrument of claim 11, wherein the bending line is formed by a thin point of the housing cladding module.

13. The medical instrument of claim 10, wherein the device further comprises a switching lug located in the portion of the housing cladding module and configured to actuate the switching element.

14. The medical instrument of claim 13, wherein the switching lug is at a distance from the switching element in the open position, as a result of which a switching path is formable.

15. The medical instrument of claim 10, wherein the switching element comprises a microswitch, the microswitch being configured to stop a movement of the carrier module.

16. The medical instrument of claim 10, wherein the housing cladding module is screwed to the carrier module at the connection site.

17. The medical instrument of claim 10, wherein the housing cladding module is a thermoplastic polymer.

18. The medical instrument of claim 10, wherein the medical instrument is a C-arm x-ray instrument.

19. A method for identifying a collision in a medical instrument with a device, the device comprising a carrier module, a housing cladding module that is detachably connected to the carrier module at a connection site, a switching element that is arranged on the carrier module adjacent to an end of the carrier module at a distance from the connection site, and a portion of the housing cladding module positioned between the connection site and an end of the housing cladding module adjacent to the switching element such that the portion of the housing cladding module has a spring-like flexible design in order to be pressed in a direction of the switching element during a collision with an object, the method comprising:

pressing the portion of the housing cladding module in a direction of the switching element as a result of the collision with the object, wherein the device moves from an open position to a closed position upon collision with the object, wherein the end of the housing cladding module adjacent to the switching element does not contact the carrier switching element in the open position, and wherein the end of the housing cladding module adjacent to the switching element contacts the switching element in the closed position; and triggering, by the switching element, a collision signal.

20. The method of claim 19, wherein the medical instrument is a C-arm x-ray instrument.

* * * * *